(12) United States Patent
Minegishi

(10) Patent No.: US 7,387,394 B2
(45) Date of Patent: Jun. 17, 2008

(54) DEFORMABLE MIRROR CONTROL DEVICE AND DEVICE FOR OBSERVING RETINA OF EYE

(75) Inventor: Isao Minegishi, Tokyo (JP)

(73) Assignee: Topcon Corporation, Tokyo (JP)

( * ) Notice: Subject to any disclaimer, the term of this patent is extended or adjusted under 35 U.S.C. 154(b) by 371 days.

(21) Appl. No.: 11/049,286

(22) Filed: Feb. 3, 2005

(65) Prior Publication Data
US 2005/0207037 A1 Sep. 22, 2005

(30) Foreign Application Priority Data
Feb. 3, 2004 (JP) .............................. 2004-027128

(51) Int. Cl.
*G02B 5/08* (2006.01)
(52) U.S. Cl. ...................................... 359/846; 359/849
(58) Field of Classification Search ................ 359/846, 359/849
See application file for complete search history.

(56) References Cited

U.S. PATENT DOCUMENTS 6,042,233 A    3/2000  Mihashi et al.
6,791,741 B2 *  9/2004  Hishioka ..................... 359/291

FOREIGN PATENT DOCUMENTS

| JP | 11-137522 A | 5/1999 |
|----|-------------|--------|
| JP | 2004-329282 A | 11/2004 |
| WO | WO 98/27863 A1 | 7/1998 |

* cited by examiner

*Primary Examiner*—Euncha P. Cherry
(74) *Attorney, Agent, or Firm*—Foley & Lardner LLP

(57) ABSTRACT

A deformable mirror control device is provided with improved response characteristic by devising the mode of control even if the deformable mirror has a large time constant in comparison with the response speed required in applications such as the retinal camera. The deformable mirror device comprises a deformable mirror 10 having a reflective surface deformed with an applied voltage, and a voltage control circuit 20 for controlling the voltage applied to the deformable mirror 10. Here, the voltage control circuit 20 produces a steady-state voltage at which the reflective surface of the deformable mirror 10 takes an intended shape in a steady state, and produces a transient voltage that causes the reflective surface of the deformable mirror 10 to deform toward the intended shape, and also produces a transient voltage that causes the shape of the reflective surface of the deformable mirror 10 to shift quickly toward the intended shape.

22 Claims, 13 Drawing Sheets

Example of electrode arrangement

Transient period

DEFORMABLE MIRROR CONTROL DEVICE AND DEVICE FOR OBSERVING RETINA OF EYE

BACKGROUND OF THE INVENTION

1. Technical Field

The present invention relates to a deformable mirror device appropriate for use in retinal cameras, heads-up displays, astronomical telescopes, laser irradiation devices and so on. The present invention also relates to a device for observing the retina of an eye that casts light beam from a photographing light source to an eye to be examined and records the image of the light beam reflected from the retina of the eye as a retinal image, for diagnosing the retina of the eye.

2. Related Art

The device such as a camera for observing the retina of an eye is used by ophthalmologists and ophthalmic opticians to photograph the image of the retina of an eye for inspecting the state of the retina, hemorrhage on the retina of the eye, and so on. Incidentally, the human eyes optical system is composed of the cornea, the lens, the vitreous body and others with, unlike an ideal optical system used as a basis of the geometrical optics, some deformation. In particular in the clinical field of ophthalmology, the image of the retina of the eye is required to be clear and of little aberration because the extent of difference of the examined eye from a normal eye is used as diagnosis information. However, because the optical system for the human eyes constituting the photographing device is not ideal, in some cases sufficient resolution cannot be achieved. Therefore, to compensate for the deformation of the wavefront of the optical system for the human eyes, the deformable mirrors using the piezoelectric effect have been in use.

However, the conventional deformable mirrors using the piezoelectric element require a high voltage applied to the piezoelectric element and needs to use, as an electronic control circuit, a piezoelectric element with a high dielectric strength that is expensive. Therefore, commercially available retinal cameras employ deformable mirrors using electrostatic attraction that can be actuated with a lower voltage in comparison with the piezoelectric type.

However, the electrostatic type of deformable mirrors is low in natural frequency (for example, about 10 Hz) and the response speed is about 100 milliseconds in time constant. Thus, the electrostatic type of deformable mirrors, because of its slow response in deformation, has had a problem of difficulty in performing real time processing to the extent required in the ophthalmic examination (for example, a response speed of about 30 milliseconds in time constant).

Another problem with the deformable mirrors is that its shape is determined with the limitation of the specifications of the instruments to which it is incorporated, and its thickness, size, and material cannot be changed freely. Another problem with the deformable mirrors is that its dynamic range for the deformation amount is determined with the specifications of the instruments to which it is incorporated, and the distance between electrodes of the electrostatic type of deformable mirrors is also determined accordingly. Therefore, the response characteristic of the electrostatic type of deformable mirrors to the applied voltage is inevitably determined. Thus, it is still another problem that no measures can be taken in the structural design to shorten the response time of the deformable mirrors, such measures as employing hard materials for the deformable mirrors, increasing the thickness of deformable member, and reducing the size of the deformable member.

The present invention is to solve the above problems. An object of the present invention is to provide a deformable mirror device with which response characteristic is improved by devising the mode of control even if the time constant of the deformable mirror is large in comparison with the response speed required in applications such as images of the retina of an eye. Another object of the present invention is to provide a device for observing the retina of an eye with which a real time processing can be performed to the extent required in ophthalmic examinations.

SUMMARY OF THE INVENTION

A deformable mirror device of the present invention accomplishing the above object is a device, for example as shown in FIG. 1, comprising a deformable mirror 10 with its reflective surface deformed with the applied voltage and a voltage control circuit 20 for controlling the voltage applied to the deformable mirror 10. Here, the voltage control circuit 20 produces a steady-state voltage at which the reflective surface of the deformable mirror 10 takes an intended shape in a steady state, and produces a transient voltage that causes the reflective surface of the deformable mirror 10 to deform toward the intended shape, and also produces the transient voltage that causes the shape of the reflective surface of the deformable mirror 10 to shift quickly toward the intended shape.

At the moment when the deformable mirror 10 is caused to deform (just after the voltage application) with the device constituted as described above, startup of deformation of the deformable mirror 10 is improved by applying the transient voltage with the voltage control circuit 20. At the moment when the intended deformation is attained, the applied voltage to the deformable mirror 10 by the voltage control circuit 20 is changed from the transient voltage to the steady-state voltage, so as to improve the response characteristic of the entire deformable mirror device provided with the deformable mirror 10.

It is preferable that, as shown in FIG. 1 for example, the voltage control circuit 20 in the deformable mirror device of the present invention is a control circuit that controls the applied voltage with a DC voltage and is constituted that the transient voltage is in the direction of increasing the deformation amount of the reflective surface of the deformable mirror 10 toward the intended shape compared to the deformation amount with the applied voltage for producing the steady-state voltage. With the above constitution, because the voltage control circuit 20 can directly control the output DC voltage, the relationship between the applied voltage and the deformation of the deformable mirror 10 is easily known by intuition.

It is preferable that, as shown in FIG. 5 for example, the voltage control circuit 20 in the deformable mirror device of the present invention is a control circuit that performs pulse width modulation (PWM) and is constituted that the transient voltage is produced with a duty ratio in the direction of increasing the deformation amount of the reflective surface of the deformable mirror 10 toward the intended shape compared to the deformation amount with the duty ratio for producing the steady-state voltage. With the above constitution, because the voltage control circuit 20 can control the output DC voltage with pulse width, it is possible to change average applied voltage without controlling the voltage level.

It is preferable that, as shown in FIG. 8 for example, the voltage control circuit 20 in the deformable mirror device of the present invention is an electric circuit having a switching circuit 26 that outputs applied voltage toward a load with switching positive and negative polarities of the applied voltage, and is a control circuit that controls the positive or negative applied voltage, and is constituted that the transient voltage is in the direction of increasing the deformation amount of the reflective surface of the deformable mirror 10 toward the intended shape compared to the deformation amount with the applied voltage for producing the steady-state voltage. With the above constitution, as the polarities of the applied voltage to the deformable mirror 10 with the voltage control device 20 are always switched with the switching circuit 26, the deformable mirror 10 does not happen to be charged in one polarity only, so that the deformed shape of the deformable mirror 10 is stabilized.

It is preferable that, as shown in FIG. 10 for example, the voltage control circuit 20 in the deformable mirror device of the present invention is a reversing circuit 28 for energizing the deformable mirror with its polarity reversed and a control circuit that performs pulse width modulation, and is constituted that the transient voltage is produced with an on-time ratio in the direction of increasing the deformation amount of the reflective surface of the deformable mirror 10 toward the intended shape compared to the deformation amount with the on-time ratio for producing the steady-state voltage. With the above constitution, as the polarity of the voltage applied with the voltage control circuit 20 to the deformable mirror 10 changes without using two, positive and negative, kinds of high voltage power sources, the deformable mirror 10 does not happen to be charged in one polarity only, so that the deformed shape of the deformable mirror 10 is stabilized. Moreover, because the voltage control circuit 20 can control the output DC voltage with pulse width modulation, it is possible to change average applied voltage without controlling the voltage level.

In a preferable constitution of the deformable mirror device of the present invention, the time determined from the time constant of the reflective surface of the deformable mirror 10 is used as the time for applying the transient voltage in the direction of increasing the deformation amount of the reflection surface of the deformable mirror 10 toward the intended shape, to shift the shape of the reflection surface of the deformable mirror 10 near the status of the intended shape, followed by voltage control with the steady-state voltage, so that switching from the transient voltage to the steady-state voltage in the voltage control circuit 20 is carried out smoothly.

The device for observing the retina of an eye according to the present invention accomplishing the above objects is, as shown in FIG. 13 for example, characterized by the use of a deformable mirror device of anyone of claims 1 to 6.

The deformable mirror device of the present invention is constituted that the voltage control circuit produces a transient voltage in the direction of increasing the deformation amount of the reflective surface of the deformable mirror 10 toward the intended shape, and then produces a steady-state voltage with which the reflective surface of the deformable mirror 10 takes the intended shape in a steady-state. Therefore, it is possible to bring the device to an intended steady state quickly in comparison with the time constant determined from the size, material, and thickness of the deformable mirror.

With the device for observing the retina of an eye according to the present invention, it is possible to translate the measurement results of the examined eye into the mirror shape in real time, which can be utilized in automatic compensation of the retinal camera.

The basic Japanese Patent Application No. 2004-027128 filed on Feb. 3, 2004 is hereby incorporated in its entirety by reference into the present application. The Japanese Patent Application No. 2003-125279 is also hereby incorporated in its entirety by reference into the present application.

The present invention will become more fully understood from the detailed description given hereinbelow. The other applicable fields will become apparent with reference to the detailed description given hereinbelow. However, the detailed description and the specific embodiment are illustrated of desired embodiments of the present invention and are described only for the purpose of explanation. Various changes and modifications will be apparent to those ordinary skilled in the art on the basis of the detailed description.

The applicant has no intention to give to public any disclosed embodiments. Among the disclosed changes and modifications, those which may not literally fall within the scope of the present claims constitute, therefore, a part of the present invention in the sense of doctrine of equivalents.

The use of the terms "a" and "an" and "the" and similar referents in the context of describing the invention are to be construed to cover both the singular and the plural, unless otherwise indicated herein or clearly contradicted by context. The use of any and all examples, or exemplary language (e.g., "such as") provided herein, is intended merely to better illuminate the invention and does not pose a limitation on the scope of the invention unless otherwise claimed.

BRIEF DESCRIPTION OF THE DRAWINGS

FIG. 2(a) shows a waveform 1 corresponding to the applied voltage, and FIG. 2(b) shows a waveform 2 corresponding to the deformation amount.

FIG. 3(a) shows a waveform 4 corresponding to applied voltage, and FIG. 3(b) shows waveforms 3 and 5 corresponding to the deformation amount.

DETAILED DESCRIPTION OF THE PREFERRED EMBODIMENT

[Principle]

Figure 1A:
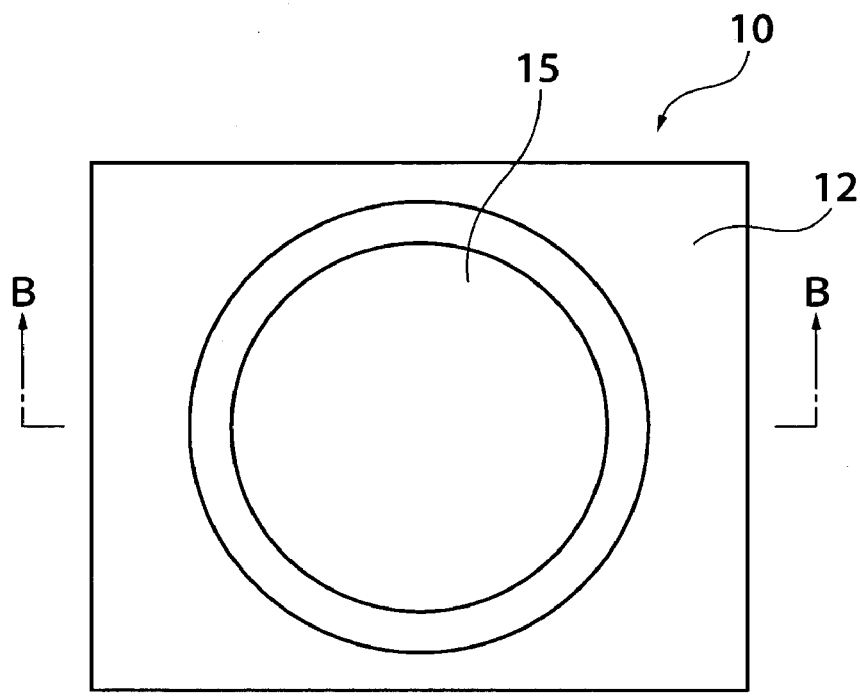
FIG. 1(a) and FIG. 1(b) show a block diagram in cross section of an example of an electrostatic type of deformable mirror together with a voltage producing circuit and a voltage control circuit.
Figure 1B:
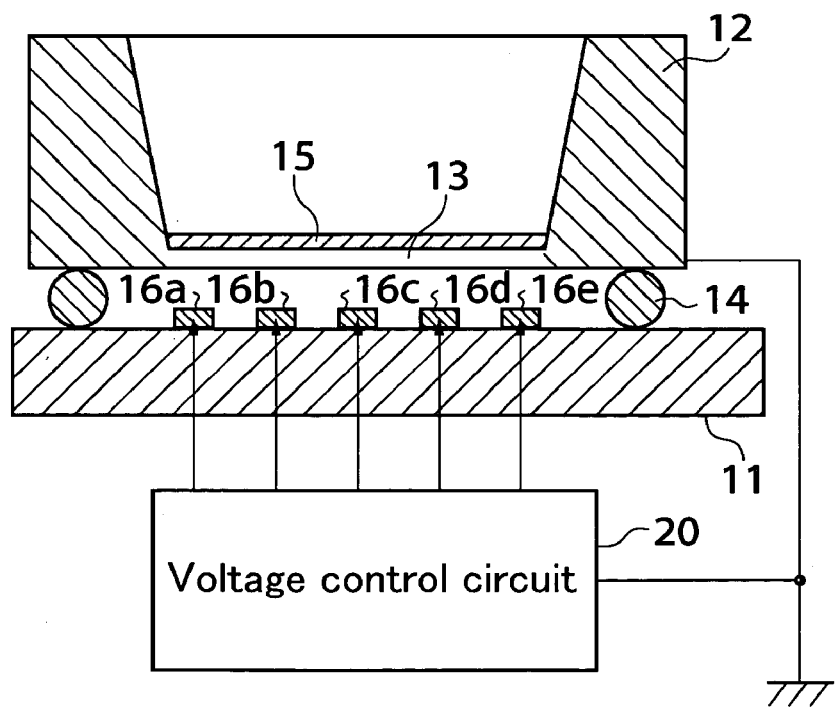

FIG. 1 is a block diagram showing an example of an electrostatic type of deformable mirror. In the figure, FIG. 1(a) is a plan view, and FIG. 1(b) is a sectional view as seen along the line B-B of FIG. 1(a) and shows a voltage control circuit also. As shown in the figures, the electrostatic type of deformable mirror 10 comprises: a glass substrate 11, a silicon substrate 12, a membrane 13, spacers 14, reflective membrane 15, and electrodes 16. The membrane 13 is produced by selective etching process of the silicon substrate 12, which is with flexibility and of a thickness of about 4 μm for example. The reflective membrane 15 is produced by vapor deposition of a high reflectivity material to the membrane 13, for example, by using a metallic material with a high reflectivity such as aluminum. The spacers 14 are used to keep the gap between the membrane 13 and the electrodes 16 at the predetermined value and are made of, for example, balls with a high rigidity. The electrodes 16 are provided in a specified number on the glass substrate 11. The electrodes 16a, 16b, 16c, 16d, and 16e are actuated individually with the voltage control circuit 20.

Figure 2A:
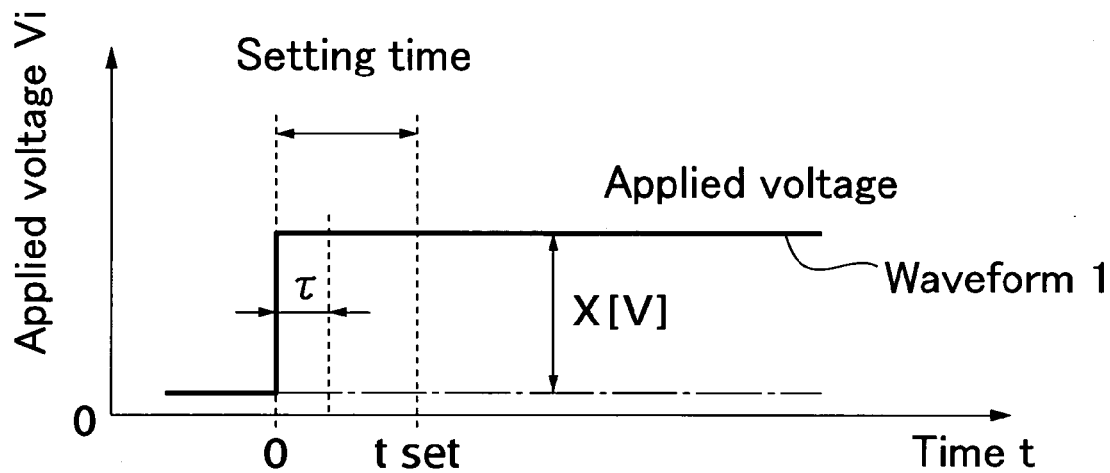
FIG. 2(a) and FIG. 2(b) show waveforms representing response curves of the reflective membrane when voltage is applied stepwise to the deformable mirror.
Figure 2B:
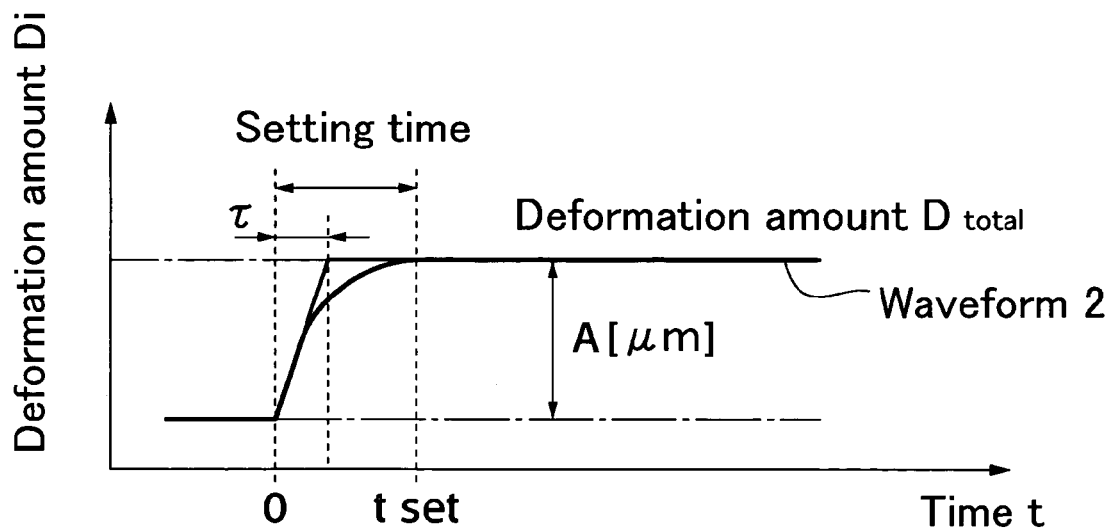

FIG. 2 shows waveforms representing response curves of the reflective membrane when voltage is applied stepwise to the deformable mirror. FIG. 2(a) shows a waveform 1 corresponding to the applied voltage. FIG. 2(b) shows a waveform 2 corresponding to the deformation amount. In FIG. 2(a), applied voltage Vi is applied stepwise as applied voltage X[V] at the time 0. FIG. 2(b) shows a measurement curve of change with time in the deformation amount Di of the membrane 13 as a response curve of a primary delay system of a time constant τ. Measurement of time t starts with the application of the stepwise voltage. With the response curve of a primary delay system, the deformation amount Di of the membrane 13 reaches about 10% of the total deformation amount $D_{total}$ at $t=τ/10$, and the deformation amount Di of the membrane 13 reaches about 63% of the total deformation amount $D_{total}$ at $t=τ$. Here, the total deformation amount $D_{total}$ of the membrane 13 shows the total deformation amount A [μm] of the reflective membrane in a balanced state for the applied voltage when a sufficient time has elapsed (for example when a setting time $t_{set}$ has elapsed) with reference to the time constant τ.

First Embodiment

Figure 3A:
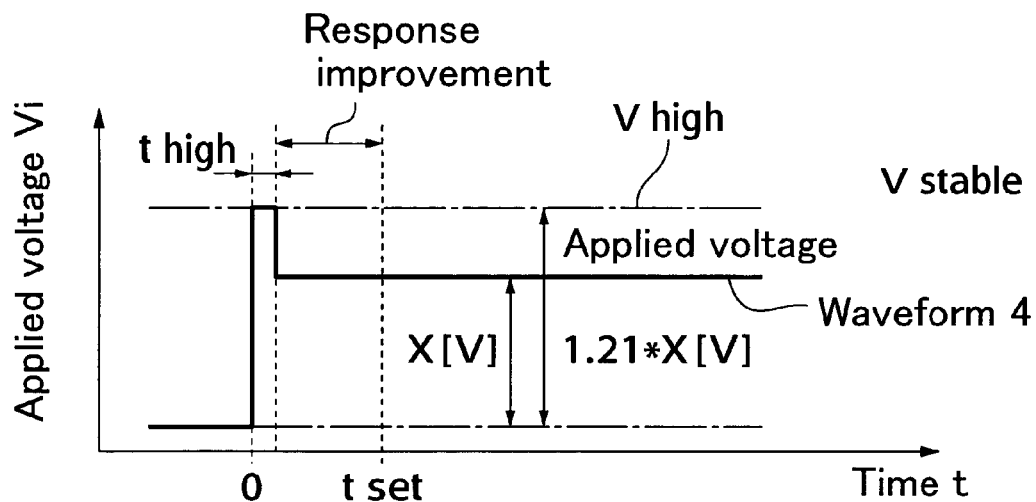
FIG. 3(a) and FIG. 3(b) show waveforms representing response curves of the reflective membrane when transient voltage and steady-state voltage are applied in succession to the deformable mirror.
Figure 3B:
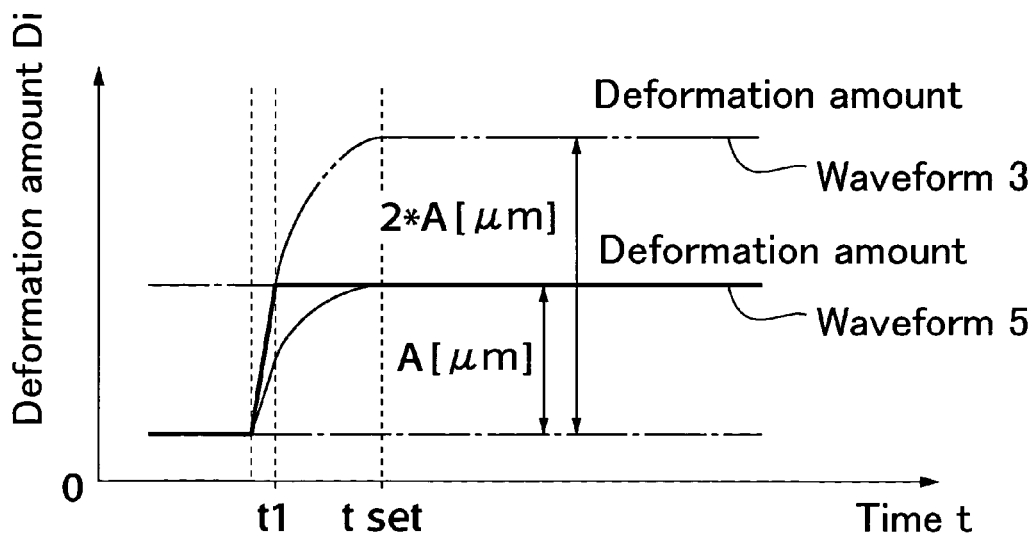

FIG. 3 shows waveforms representing response curves of the reflective membrane when transient voltage and steady-state voltage are applied in succession to the deformable mirror. FIG. 3(a) shows a waveform 4 corresponding to applied voltage. FIG. 3(b) shows waveforms 3 and 5 corresponding to the deformation amount. As shown in FIG. 3(a), the applied voltage Vi is a high voltage $V_{high}$ for the period of time between 0 and $t_{high}$, and is a steady-state voltage $V_{stable}$ for the period of time after $t_{high}$. In FIG. 3(b), the waveform 3 in a dash-and-single-dotted line shows step response to the high voltage $V_{high}$, and the waveform 5 in thin solid line shows the step response to the steady-state voltage $V_{stable}$. The deformation amount Di of the membrane 13 is shown with: the waveform 3 for the period of time between 0 and $t_{high}$, the curve interconnecting the waveforms 3 and 5 for the period of time between $t_{high}$ and the setting time $t_{set}$, and the waveform 5 after the setting time $t_{set}$.

With the device of the above constitution, the voltage control circuit 20 applies a high voltage $V_{high}$ as a transient voltage to the membrane 13 at the time 0 at which deformation of the membrane 13 is started. Thereupon, the deformation of the membrane 13 starts up more steeply than with the steady-state voltage $V_{stable}$ and an intended deformation is attained with the lapse of the response time $t_{high}$. Next, at the time $t_{high}$, the voltage control circuit 20 sets the applied voltage again to the steady-state voltage $V_{stable}$. This improves response characteristic of the deformable mirror 10 with a higher response speed. Here, the response time $t_{high}$ is determined to be a time at which the response deformation amount Di of the membrane 13 with the high voltage $V_{high}$ reaches the total deformation amount $D_{total}$ of the membrane 13 for the steady-state voltage $V_{stable}$. Incidentally, the response time $t_{high}$ may be set for example to about 80% to 90% of theoretical response time to prevent the response deformation amount Di of the membrane 13 from overshooting its target, the total deformation amount $D_{total}$.

Next, the relationship between the applied voltage Vi and the deformation amount Di of the membrane 13 is described. The relationship between the applied voltage Vi and the deformation amount Di is expressed with the equation (1).

$$k \cdot Di = \epsilon_0 \cdot S \cdot Vi^2/2 \cdot (dg-Di)^2 \tag{1}$$

where dg represents the gap length, k the spring constant, Di the deformation amount of the membrane 13, S the surface area, Vi the applied voltage, and $\epsilon_0$ the dielectric constant of vacuum. For example, in case that the gap length dg is 40 μm and the deformation amount Di is assumed to be increased from 5 μm to 10 μm as the total deformation amount $D_{total}$ of the membrane 13 in steady state, the applied voltage $V_{10}$ for 10 μm relative to the applied voltage $V_5$ for 5 μm needs to satisfy the following relationship.

$$V_{10}/V_5 = 1.21 \tag{2}$$

For example, a deformable mirror 10, made of single crystal silicon, of a round shape of 15 mm in diameter and 4 μm in thickness is operated with the voltage control circuit 20 applying 50[V] as the applied voltage X[V]. Then, the total deformation amount $D_{total}$ of the membrane 13 becomes 5 μm, the response waveform becomes as shown in FIG. 2(b), and the setting time for reaching the total deformation amount $D_{total}$ is about 200 milliseconds. Here, for doubling the total deformation amount $D_{total}$ of the membrane 13 from 5 to 10 μm, 60.5[V] as the applied voltage X[V] is applied according to the equation (2) with the voltage control circuit 20. The response time $t_{high}$ becomes very short, for example about 30 milliseconds.

Figure 4:
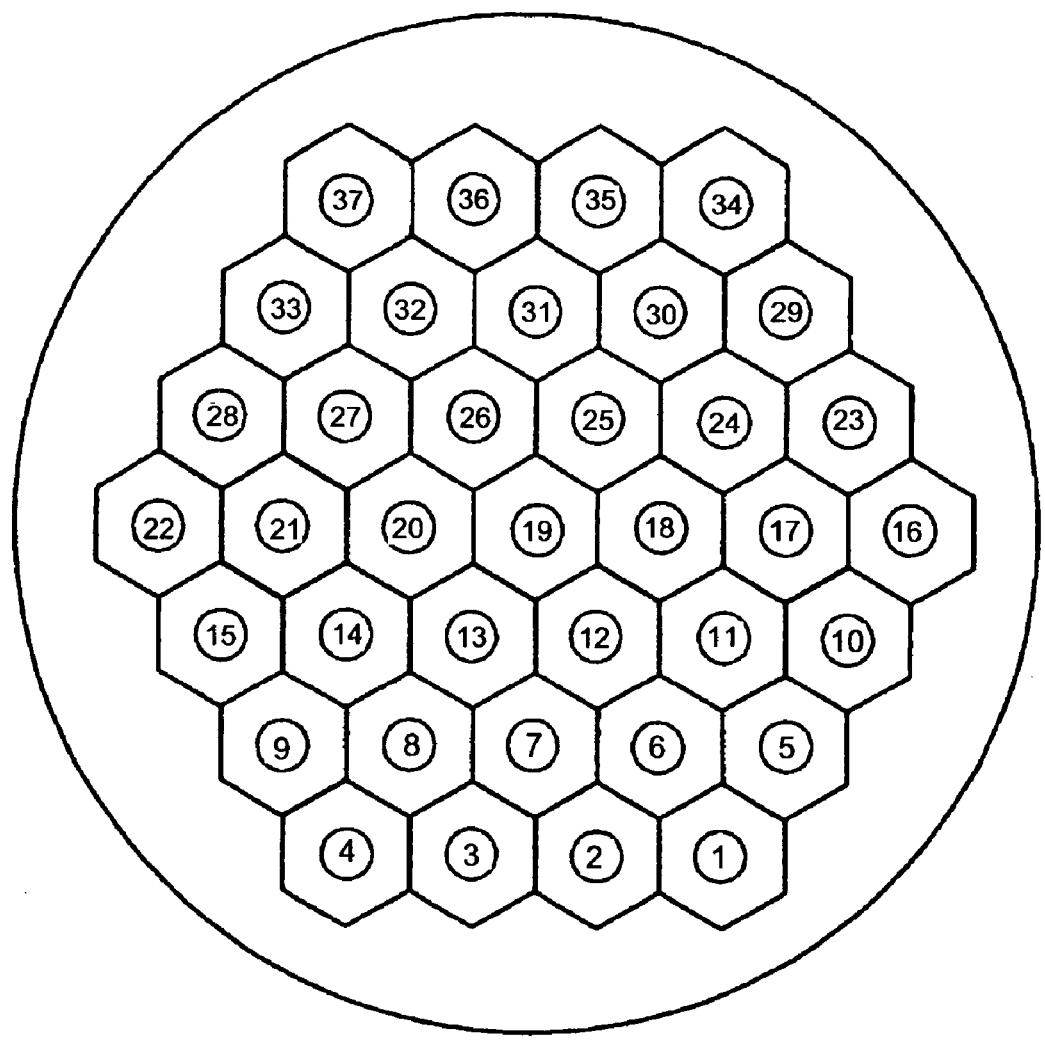
FIG. 4 is a plan view for explaining the electrode array of the deformable mirror.

FIG. 4 is a plan view for explaining the electrode arrangement of the deformable mirror. Electrodes of the deformable mirror, 37 pieces including 1st to 37th, each in hexagonal shape, are arranged in a honeycomb shape, to which for example electrostatic voltage is applied to produce corresponding deformation to each electrode.

Second Embodiment

With the embodiment 1, it is explained that the response characteristic is improved by controlling the applied voltage. In this second embodiment, a linear voltage control of several hundred volts is performed to control the applied voltage level of the voltage control circuit 20. Therefore, sophisticated voltage control technique is used. In order to enhance the shaping resolution of the deformable mirror 10, the number of electrodes is increased. Voltage control is performed individually to each electrode (channel) shown in FIG. 4.

Figure 5:
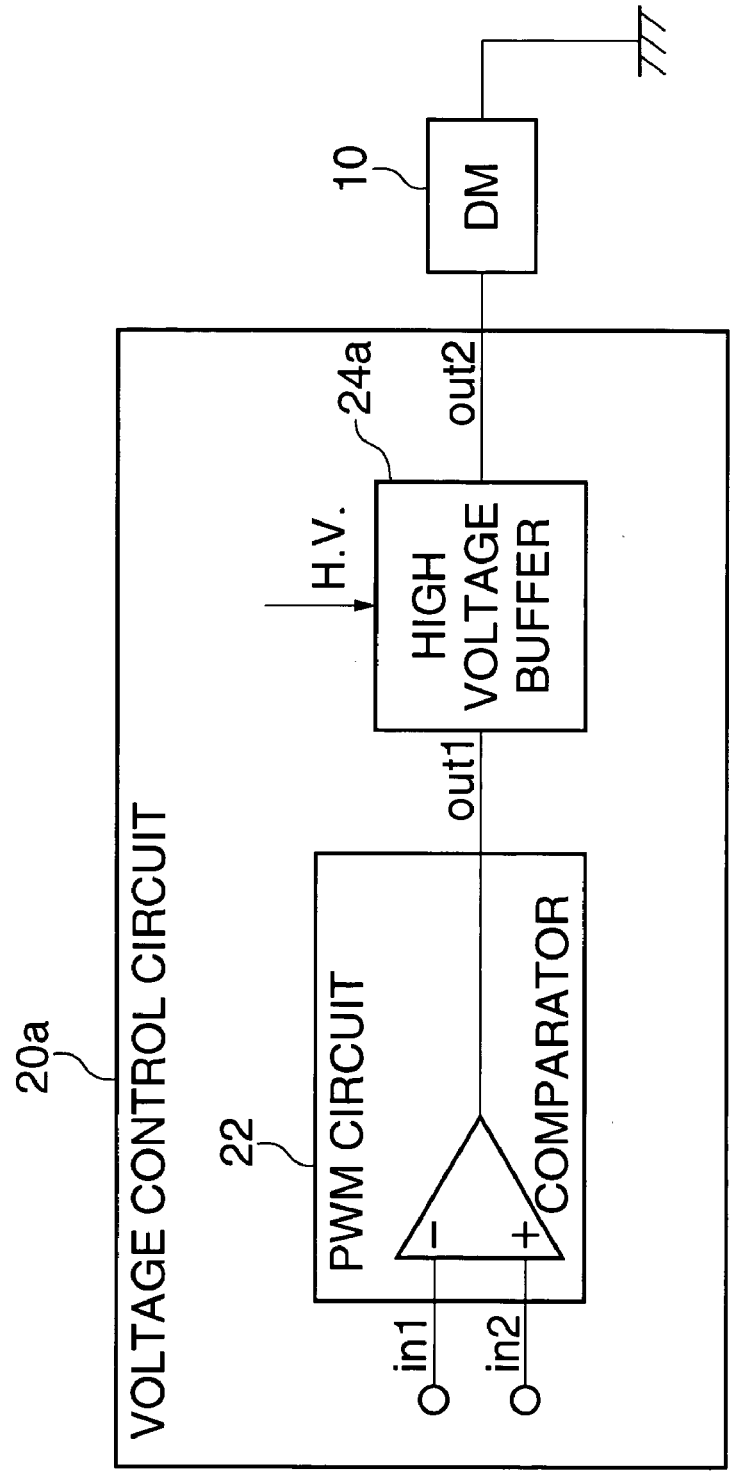
FIG. 5 is a block diagram for explaining the second embodiment of the present invention.
Figure 6A:
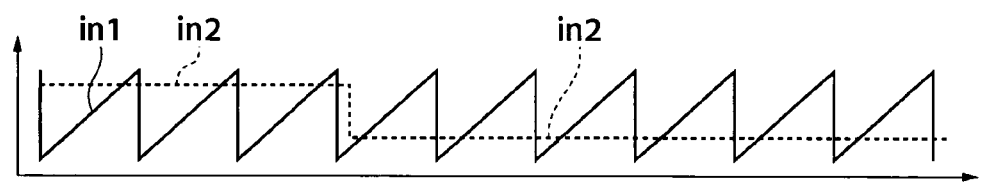
FIG. 6(a) to FIG. 6(c) are waveforms diagram for explaining the function of the device shown in FIG. 5.
Figure 6B:
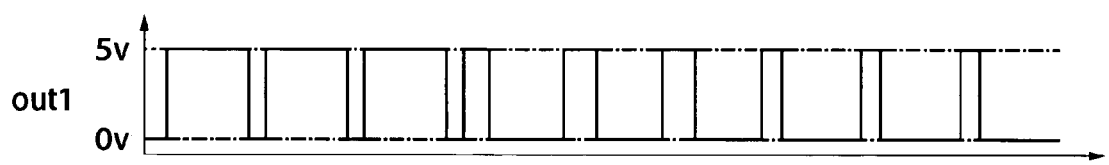
Figure 6C:
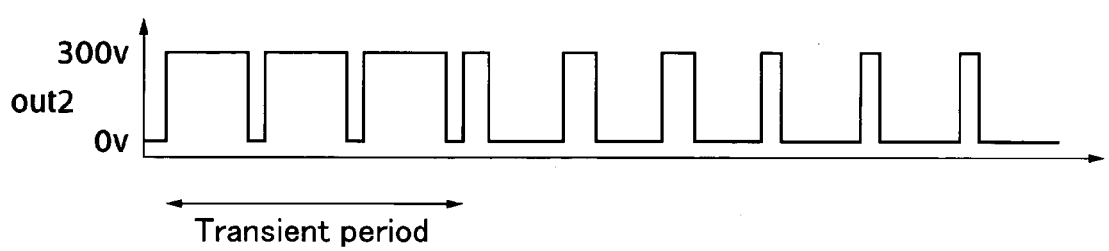

FIG. 5 is a block diagram for explaining the second embodiment of the present invention. FIG. 6 is a waveform diagram for explaining the function of the device shown in FIG. 5. In FIG. 6, (a) shows saw-tooth-shape input signal in1 and rectangular wave signal in2, (b) shows output signal out1 of a comparator 22, and (c) shows output signal out2 of a high voltage buffer circuit 24. The second embodiment employs a constitution in which the applied voltage level of the voltage control circuit 20 is not controlled directly, but is controlled by changing the average voltage through controlling the pulse width of a switching element where the pulse width modulation technique is applied. With such a constitution, circuit constitution is made simpler than in the first embodiment even when evenly performing voltage control for multiple channels.

A voltage control circuit 20a comprises a comparator 22, and a high voltage buffer circuit 24a. To the comparator 22 are inputted a saw-tooth-shape input signal in1, and a rectangular wave signal in2 as a duty ratio control signal. Depending on the signal level of the rectangular wave signal in2, the comparator 22 slices the saw-tooth-shape input signal in1 and outputs a high duty ratio output signal out1 for the period in which the signal level of the rectangular wave signal in2 is high (transient period) and a low duty ratio output signal out1 for the period in which the signal level of the rectangular wave signal in2 is low, to the high voltage buffer circuit 24a. A high voltage HV is supplied from a high voltage power source (not shown) to the high voltage buffer circuit 24a. There, the output signal out1 is amplified as an output signal out2 which is applied to the deformable mirror 10. The logical voltage level is amplified by several tens times into the voltage for energizing, and for example, for the output signal out1 of 5 V, the output signal out2 is 300 V.

Figure 7A:
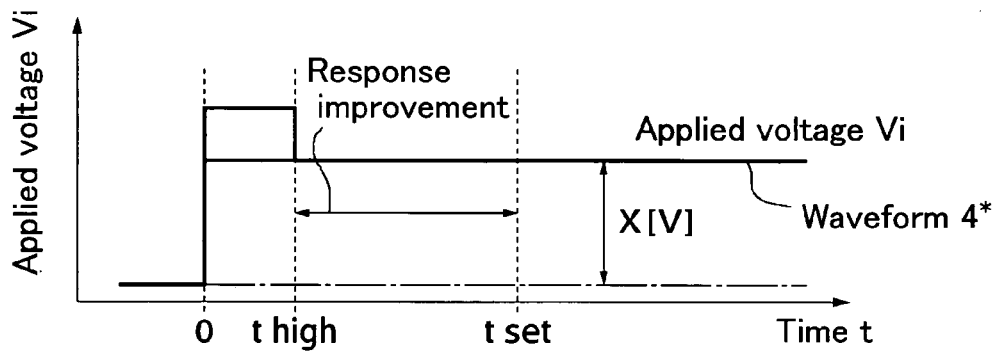
FIG. 7(a) to FIG. 7(c) show waveforms representing response curves of the reflective membrane when transient voltage and steady-state voltage are applied in succession to the deformable mirror of the second embodiment.
Figure 7B:
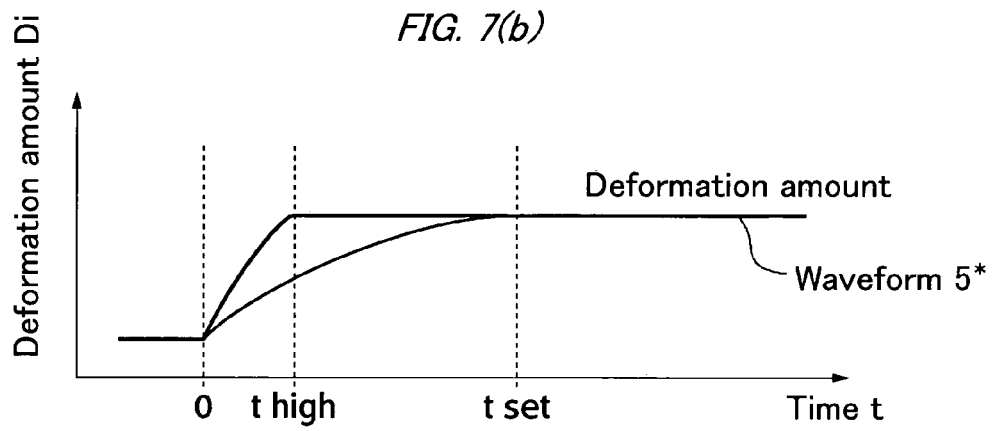
Figure 7C:
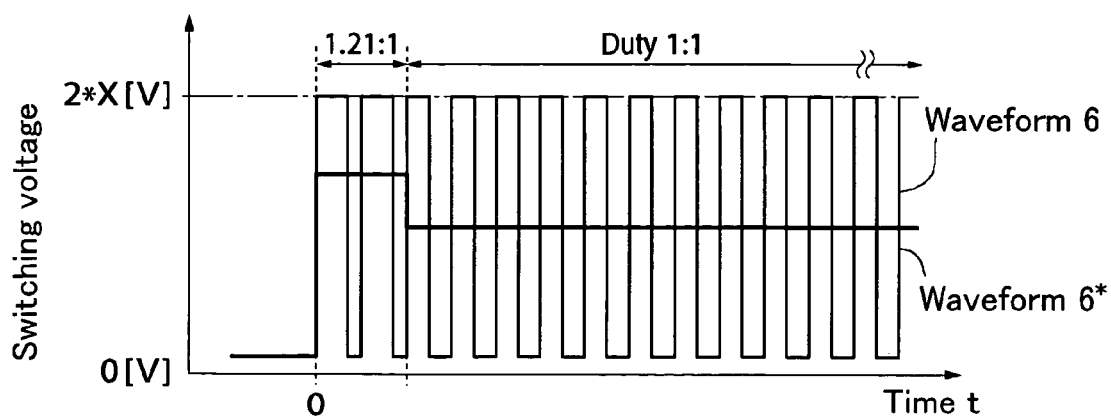

FIG. 7 shows waveforms representing response curves of the reflective membrane when transient voltage and steady-state voltage are applied in succession to the deformable mirror of the second embodiment. In FIG. 7, (a) shows a waveform 4* corresponding to the applied voltage, (b) shows a waveform 5* corresponding to the deformation amount, and (c) shows the waveforms 6, 6* corresponding to the switching voltage. In FIG. 7(a), the applied voltage Vi is the high voltage $V_{high}$ for the period of time between 0 and $t_{high}$ and becomes the steady-state voltage $V_{stable}$ after the time $t_{high}$. In FIG. 7(b), the deformation amount Di of the membrane 13 is indicated with: a step response curve corresponding to the high voltage $V_{high}$ for the period of time between 0 and $t_{high}$, a straight line of the total deformation amount $D_{total}$ for the period of time between $t_{high}$ and $t_{set}$, and a step response curve corresponding to the steady-state voltage $V_{stable}$ after the setting time $t_{set}$. In FIG. 7(c), duty ratio of the switching signal indicated with the waveform 6 is high for the period of time between 0 and $t_{high}$, and low after the time $t_{high}$. In case the duty ratio for the steady-state voltage $V_{stable}$ is, for example, 1:1, the duty ratio for the high voltage $V_{high}$ becomes, for example, 1.21:1. The waveform 6* indicates an output voltage signal produced by rectifying and smoothing the switching signal indicated with the waveform 6, and corresponds to the waveform 4*.

Third Embodiment

Figure 8:
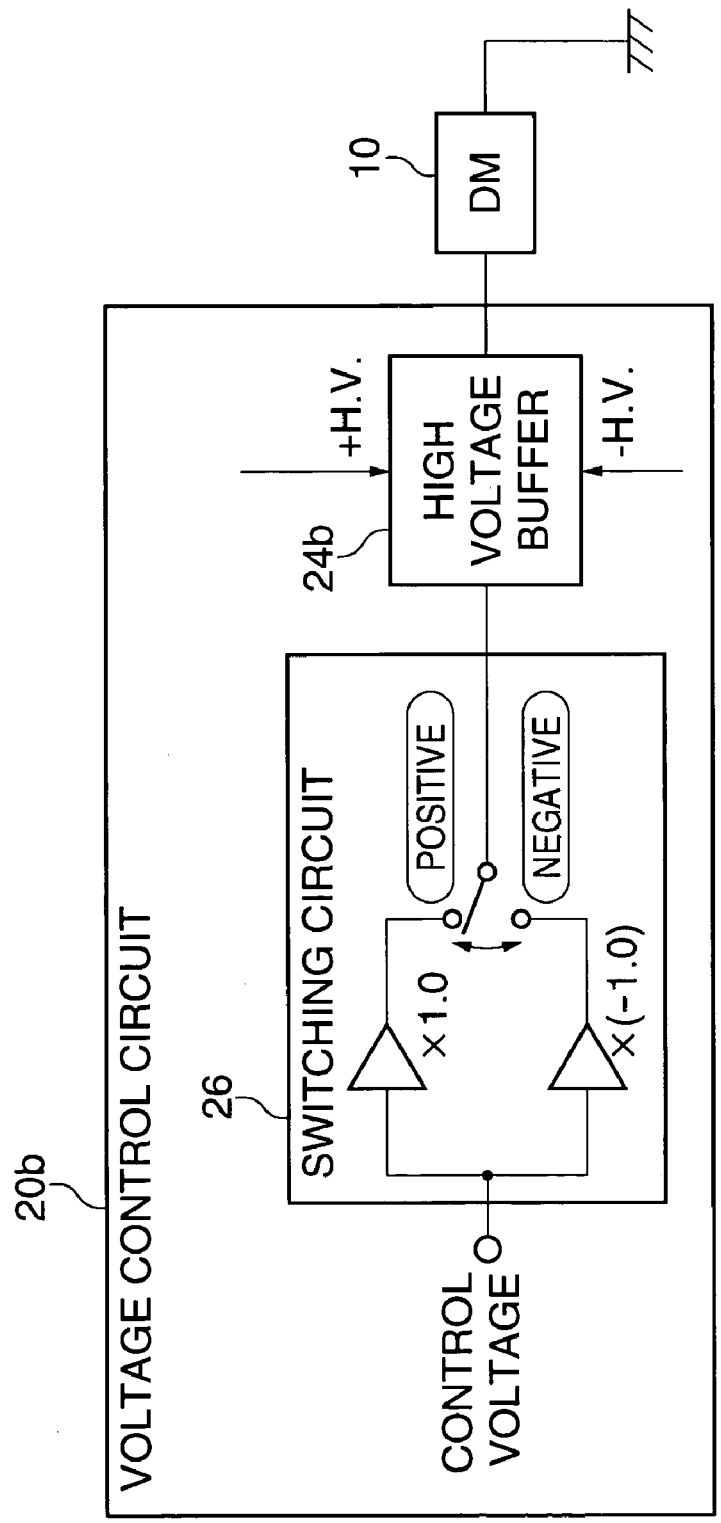
FIG. 8 is a block diagram of a voltage control circuit for explaining the third embodiment of the present invention.

FIG. 8 is a block diagram of a voltage control circuit for explaining the third embodiment of the present invention. The voltage control circuit 20b comprises a switching circuit 26 for outputting applied voltage toward a load with switching positive and negative polarities of the applied voltage, and a high voltage buffer circuit 24b. The high voltage buffer circuit 24b has a positive voltage DC source section and a negative voltage DC source section as a high voltage power source for supplying high voltage HV. The switching circuit 26 is a control circuit for controlling the polarity of the applied voltage. It is preferable to constitute the switching circuit 26 so that the transient voltage is in the direction of increasing the deformation amount of the reflective surface of the deformable mirror 10 toward the intended shape compared to the deformation amount with the applied voltage for producing the steady-state voltage. With this constitution, the polarities of the applied voltage with the voltage control circuit 20b to the deformable mirror 10 are always changed with the switching circuit 26. Therefore, the deformable mirror 10 does not happen to be charged in one polarity only, so that the deformed shape of the deformable mirror 10 is stabilized.

Figure 9A:
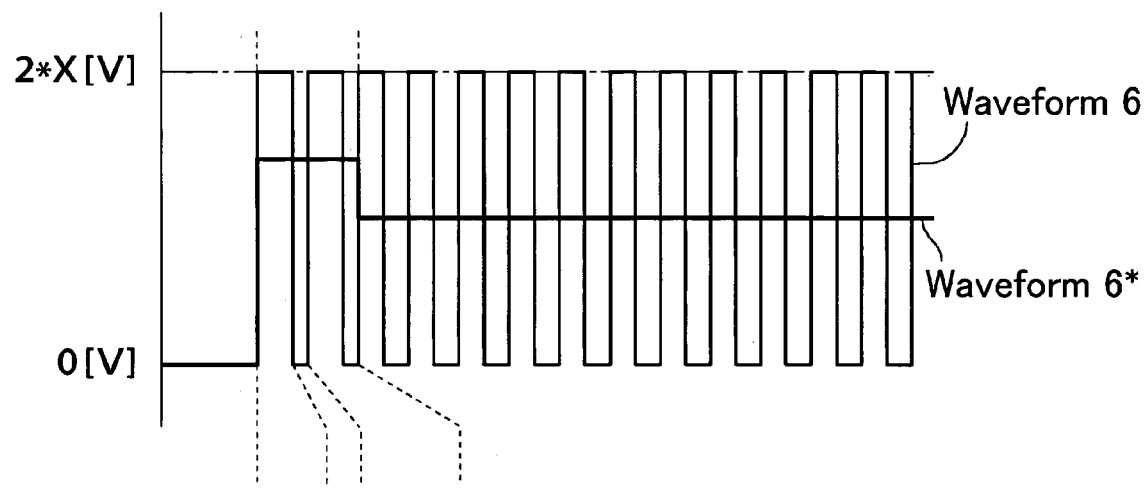
FIG. 9(a) and FIG. 9(b) show switching voltage waveforms for applying voltage stepwise to the deformable mirror of the third embodiment.
Figure 9B:
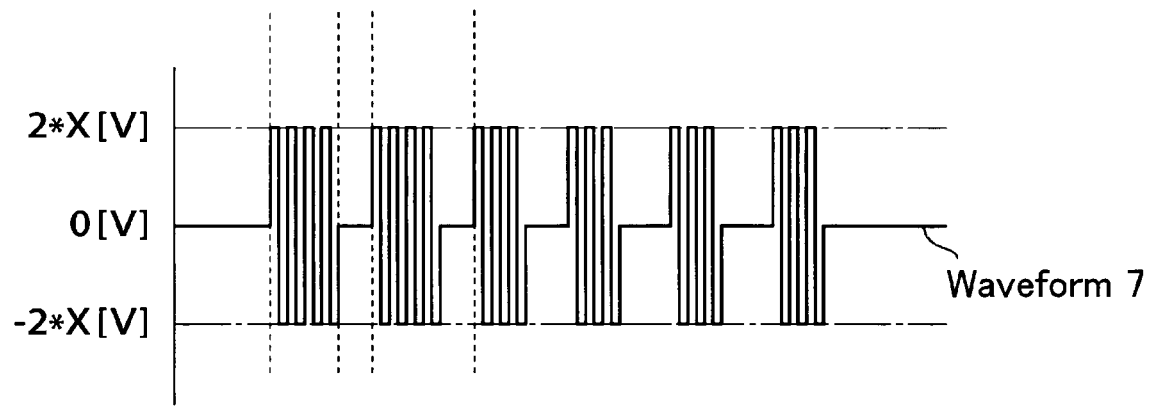

In the above constitution, when voltage with its polarity switched in a sufficiently rapid cycle relative to the response time of the deformable mirror 10 is applied between the electrodes 16 and the membrane 13, electrostatic attraction occurs between them without incurring charge-up and the membrane 13 deforms into a concave shape. FIG. 9 shows switching voltage waveforms when voltage is applied stepwise to the deformable mirror. In FIG. 9, (a) shows waveforms 6, 6* corresponding to the switching voltage of FIG. 7(c), and (b) shows an applied DC voltage waveform 7 with the high voltage buffer circuit 24b. The waveform 7 is shown with its period enlarged in comparison with the period of the waveform 6. In other words, an operation is possible in which anti-charge-up measures for the deformable mirror 10 is realized by using the control of high pulse voltage with both polarities as indicated with the waveform 7.

By the way, while the third embodiment of FIG. 8 is described as an example having both the positive voltage DC source section and the negative voltage DC source section as the high voltage power source for the high voltage buffer circuit 24b, the circuit constitution is simplified if the anti-charge-up measures for the deformable mirror 10 is realized with the positive voltage DC source section only.

Figure 10:
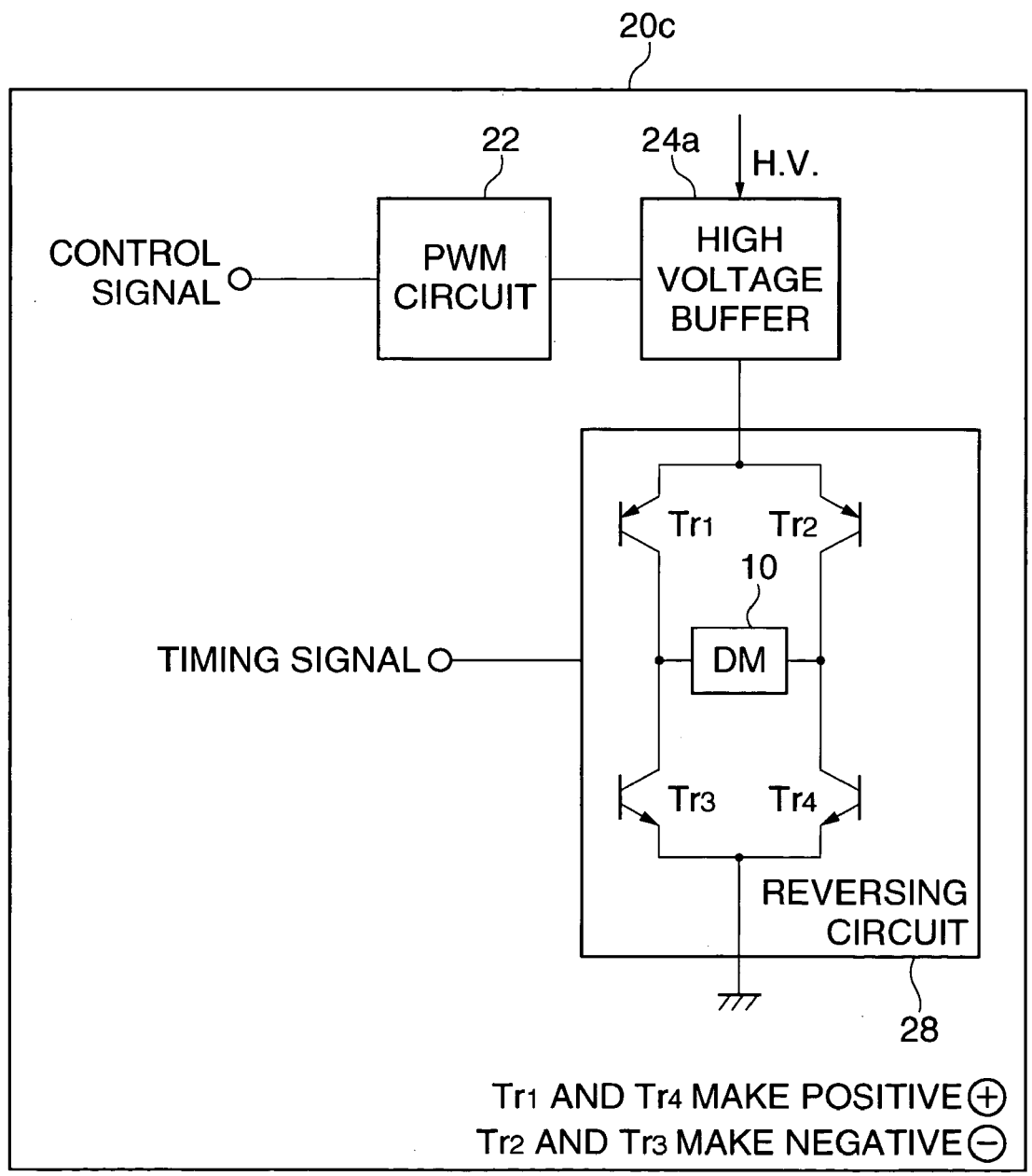
FIG. 10 is a block diagram of a voltage control circuit for explaining an exemplary modification of the third embodiment of the present invention.

FIG. 10 is a block diagram of a voltage control circuit for explaining an exemplary modification of the third embodiment of the present invention. As shown in the figure, the voltage control circuit 20 comprises: a PWM (pulse width modulation) circuit 22, a high voltage buffer circuit 24a, and a reversing circuit 28 for energizing the deformable mirror 10 as reversing the polarity. The reversing circuit 28 has four transistors Tr1, Tr2, Tr3, and Tr4 so that polarity of voltage for energizing the deformable mirror 10 is reversed with timing signals supplied from outside. Here, the transistors Tr1 and Tr4 work as the positive side while Tr2 and Tr3 as the negative side. The PWM (pulse width modulation) circuit 22 for example uses a comparator as shown in FIG. 5 to receive the saw-tooth-shape input signal in1 and the rectangular wave signal in2 as duty ratio control signal.

The above constitution makes it possible to realize measures against charge-up of the deformable mirror 10 using the reversing circuit 28 even if the high voltage source of the high voltage buffer circuit 24a includes the positive voltage DC source only.

Fourth Embodiment

Figure 11A:
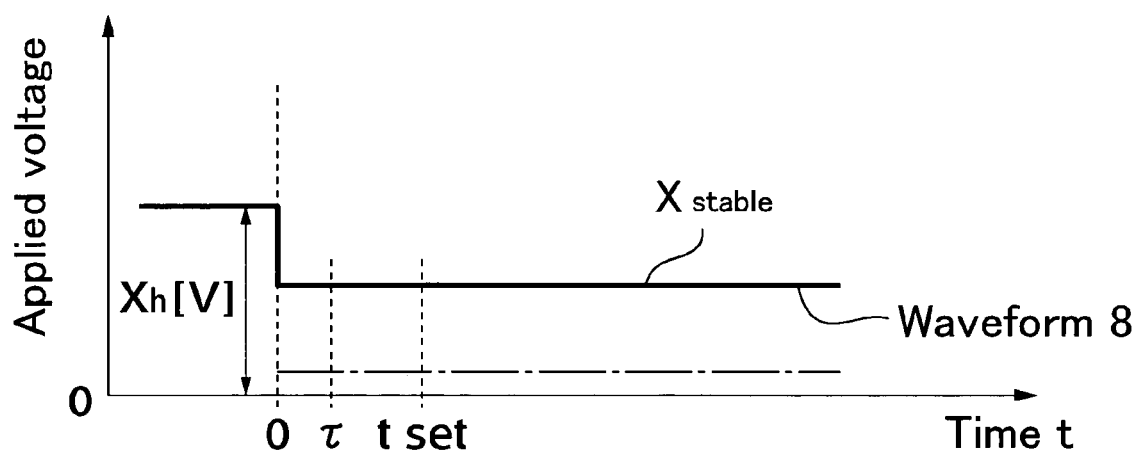
FIG. 11(a) and FIG. 11(b) show waveforms representing response curves of the reflective membrane when voltage is applied stepwise to the deformable mirror of the fourth embodiment.
Figure 11B:
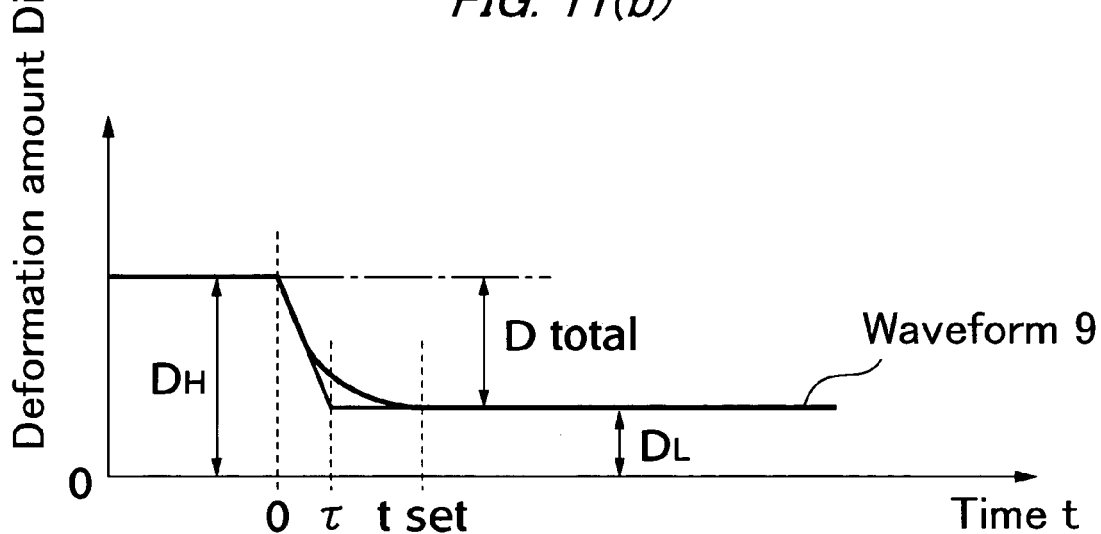

FIG. 11 shows waveforms representing response curves of the reflective membrane when voltage is applied stepwise to the deformable mirror. In FIG. 11, (a) shows a waveform 8 corresponding to applied voltage, and (b) shows a waveform 9 corresponding to the deformation amount. In FIG. 11(a), the applied voltage Vi is a high applied value $X_h[V]$ at first, and from the time 0, it is stepped down to $V_{stable}$. FIG. 11(b) shows a measurement curve of change with time in the deformation amount Di of the membrane 13, that is, a response curve of primary delay system of the time constant τ. Measurement of time t starts when the applied voltage is stepped down to the low voltage $X_l[V]$. Here, the total deformation amount $D_{total}$ appearing on the membrane 13 by the change in the applied voltage from the high $X_h[V]$ to the steady-state $V_{stable}$ is shown as that of the reflective membrane in an equilibrium state relative to the applied voltage changed, appearing at the time when a sufficient period of time has elapsed (for example when the setting time $t_{set}$ has elapsed) with reference to the time constant τ.

Figure 12A:
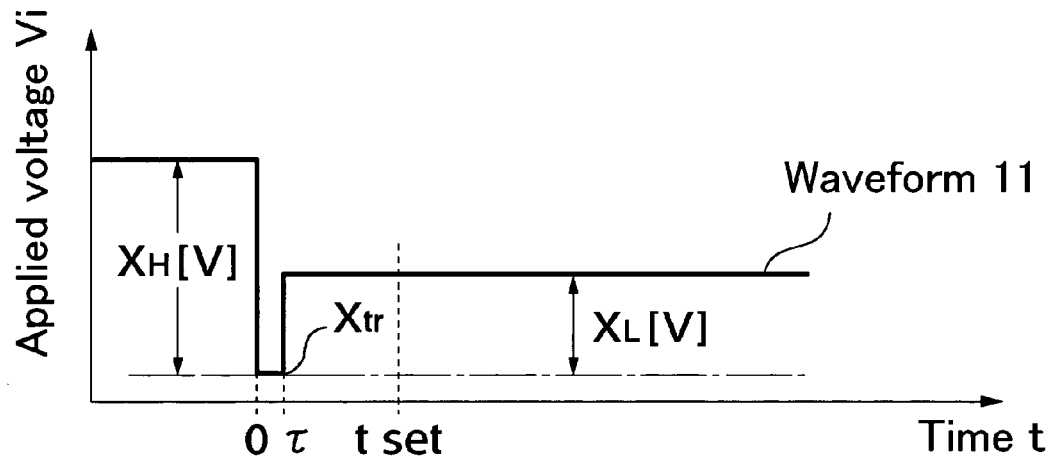
FIG. 12(a) and FIG. 12(b) show waveforms representing response curves of the reflective membrane when transient voltage and steady-state voltage are applied in succession to the deformable mirror of the fourth embodiment.
Figure 12B:
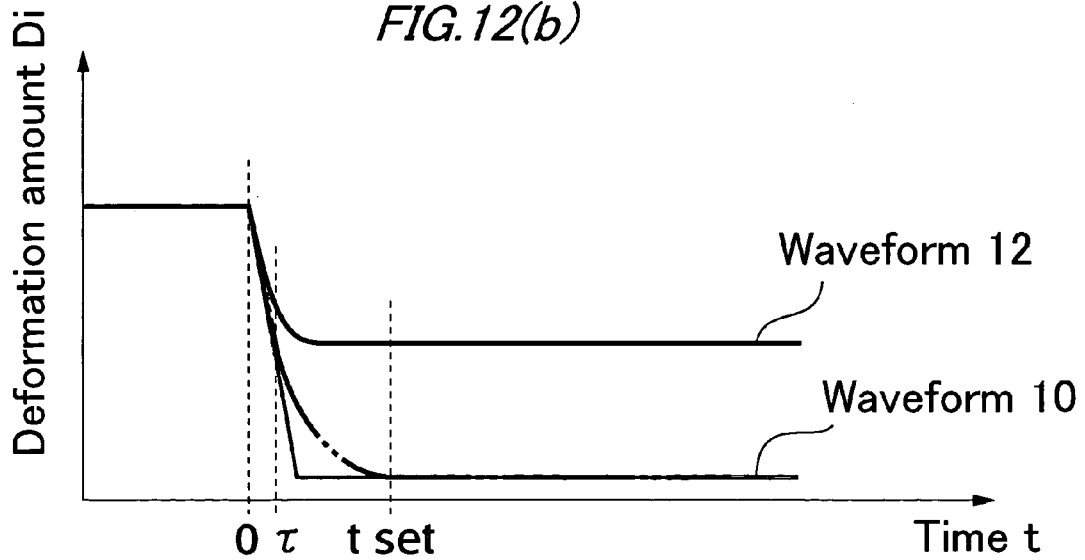

FIG. 12 shows waveforms representing response curves of the reflective membrane when the transient voltage and the steady-state voltage are applied in succession to the deformable mirror. In FIG. 12, (a) shows a waveform 11 corresponding to the applied voltage and (b) shows waveforms 10, 12 corresponding to the deformation amount. As shown in FIG. 12(a), the applied voltage Vi is a high applied voltage $X_H[V]$ at first, followed by a low transient applied voltage $X_{tr}$ for the period of time between 0 and τ, and after the time τ, a steady-state $V_{stable}$ ($X_L$) which is higher than the transient applied voltage $X_{tr}$. In FIG. 12(b), the waveform 10 in a dash-and-double-dotted line shows the step response to the low applied voltage $X_{tr}$, and the waveform 12 in solid line shows the step response to the steady-state voltage $V_{stable}$ ($X_L$) The deformation amount Di of the membrane 13 is indicated with: the waveform 10 for the period of time between 0 and τ, the curve interconnecting the waveforms 10 and 12 for the period of time between τ and the setting time $t_{set}$, and the waveform 12 after the setting time $t_{set}$.

With the above constitution, the voltage control circuit 20 using a function of its transient applied voltage control, applies a low transient applied voltage $X_{tr}$ to the membrane 13 at the time 0 when the deformation of the membrane 13 is started. Thereupon, the deformation rate of the membrane 13 is rapid in comparison with that produced with the steady-state voltage $V_{stable}$ and the intended deformation is attained after the lapse of the response time τ. Next, the voltage control circuit 20 using a function of its steady-state voltage control, sets the applied voltage again to the steady-state voltage $V_{Stable}$ at the time τ. Then, the deformation amount of the deformable mirror 10 quickly shifts into the amount of the reflective surface of the steady-state and is stabilized. In this way, response characteristic of the deformable mirror 10 is improved to be quick. Here, the response time $t_{tr}$ is set, according to the low transient applied voltage $X_{tr}$, to the time at which the response deformation amount Di of the membrane 13 reaches the total deformation amount $D_{total}$ of the membrane 13 with the steady-state voltage $V_{stable}$. Further, in order to prevent the response deformation amount Di of the membrane 13 from overshooting its target or the total deformation amount $D_{total}$, the response time $t_{tr}$ may be set to be slightly shorter, for example 70% to 100% of theoretical response time, preferably 80% to 90%.

Figure 13:
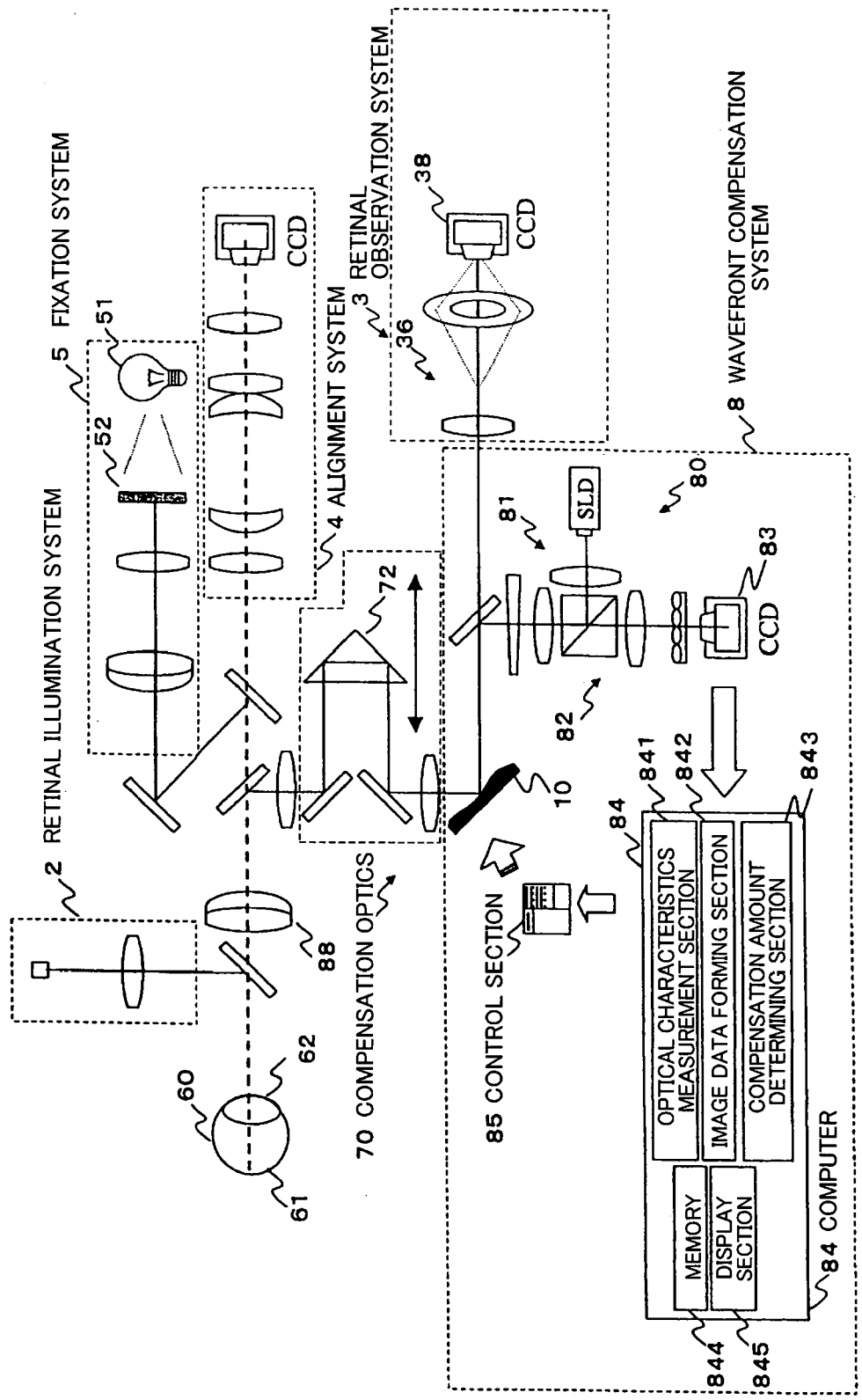
FIG. 13 is a block diagram for explaining the entire device for observing the retina of an eye.

Next, a device employing the above deformable mirror 10 for observing the retina of an eye is described. FIG. 13 is a block diagram for explaining the entire device for observing the retina of an eye. As shown in FIG. 13, the device for observing the retina of an eye comprises: a wavefront compensation system 8, a retinal illumination system 2, a retinal observation system 3, an alignment system 4, a fixation system 5, and a compensation optics 70. The wavefront compensation system 8 has: a wavefront measuring system 80 including a point image projection optical system 81, a point image reception optical system 82, and a point image receiving section 83 (CCD); a computer 84; and a control section 85. The computer 84 includes: an optical characteristic measuring section 841, an image data forming section 842, a compensation amount determining section 843, a memory 844, and a display section 845.

The retinal illumination system 2 includes: a second light source section, a condenser lens, and a beam splitter, to cast the second light beam of the second light source section to a specified area on the retina of an examined eye. The retinal observation system 3 includes a retinal image forming optical system 36 and a retinal image receiving section 38 (CCD). The retinal image forming optical system 36 includes for example an afocal lens 88, a compensation optics 70, a condenser lens, and a beam splitter, to guide the light reflected from the retina 61 through the compensation optics 70 to the retinal image receiving section 38. The compensation optics 70 has: the deformable mirror 10 for compensating aberration of measurement light, and movable prism and spherical lens that move in the optical axis direction to compensate spherical components of the aberration. The compensation optics 70 is placed in the point image projection optical system 81 and the retinal image forming optical system 36 to compensate aberration of the light beam reflected back for example from the examined eye 60.

The alignment system 4 includes a condenser lens and an alignment light receiving section to guide the light beam emitted from the light source section and coming back as reflected from the cornea 62 of the examined eye 60 to the alignment light receiving section. The fixation system 5 includes a light path for casting a target for fixation and fogging of the examined eye 60 for example, and has a third light source section 51, a fixation target 52, and a relay lens. It is possible to cast the fixation target 52 with the light beam from the third light source 51 to the retina 61 so that the examined eye 60 observes the image.

The optical characteristic measuring section 841 determines optical characteristics including aberration of higher orders of the examined eye 60 according to the output from the point image receiving section 83. The image data forming section 842 carries out simulation of perceived state of the target according to the optical characteristics, and calculates data of the examined eye such as MTF indicating the perceived state or simulation image data. The memory 844 stores a plurality of voltage change templates for adjusting the deformable mirror 10. The compensation amount determining section 843 chooses from the voltage change templates stored in the memory 844 and, determines a compensation amount for the deformable mirror 10 according to the voltage change template chosen, and outputs the compensation amount to the control section 85. The control section 85 deforms the deformable mirror 10 according to the output from the compensation amount determining section 843. Further details of the device for observing the retina of an eye are described for example in the specification of a Japanese patent application No. 2003-125279 relating to the proposal of the applicant of the present invention.

In the above embodiment, the device employing the deformable mirror is described as the device for observing the retina of an eye. However, there are many devices employing the deformable mirror, including the head-up display, the astronomical telescope, the laser irradiation device, and so on.

DESCRIPTION OF REFERENCE NUMERALS

10: Deformable mirror
20: Voltage control circuit
22: Comparator (PWM circuit)
24: High voltage buffer circuit
26: Switching circuit
28: Reversing circuit

What is claimed is:

1. A deformable mirror device comprising:
    a deformable mirror with a reflective surface deformed with an applied voltage; and
    a voltage control circuit for controlling the applied voltage,
    wherein the voltage control circuit has functions of producing a steady-state voltage at which the reflective surface of the deformable mirror takes a predetermined shape in a steady state and of changing the applied voltage into a transient voltage which is of a voltage change greater than a change of the steady-state voltage to a direction of the voltage change during a first part of a transient period in which the deformable mirror deforms into the predetermined shape, and of changing the applied voltage into the steady-state voltage during a second part of the transient period that occurs after the first part of the transient period, for causing the reflective surface of the deformable mirror to deform quickly toward the predetermined shape.

2. The deformable mirror device of claim 1, wherein the voltage control circuit is a control circuit that controls the applied voltage to the deformable mirror with a DC voltage, wherein the direction of the voltage change is such that the transient voltage is of a lesser voltage value than the steady-stage voltage.

3. The deformable mirror device of claim 1, wherein the voltage control circuit is: a control circuit that controls the applied voltage to the deformable mirror with a DC voltage and has a switching element for turning on and off the DC voltage; and
    a control circuit that performs pulse width modulation by applying on- and off-control signals to the switching element, where the transient voltage is produced with a duty ratio of the direction in which a deformation amount of the reflective surface of the deformable mirror increases toward the intended shape compared to the deformation amount with the duty ratio for producing the steady-state voltage.

4. The deformable mirror device of claim 1, wherein the voltage control circuit is a control circuit that controls the deformable mirror with positive and negative applied voltage, and has a switching circuit for outputting applied voltage toward a load with switching positive and negative polarities of the applied voltage; and
    the transient voltage is of the direction in which the deformation amount of the reflective surface of the deformable mirror increases toward the intended shape compared to the deformation amount with the applied voltage for producing the steady-state voltage.

5. The deformable mirror device of claim 1, wherein the voltage control circuit is: a control circuit that controls the deformable mirror by positive and negative applied voltage and has a switching circuit for outputting applied voltage toward a load with switching positive and negative polarities of the applied voltage and a switching element for positive and negative for turning on and off the positive or negative applied voltage; and
    a control circuit that performs pulse width modulation by applying on- and off-control signals to the switching element, where the transient voltage is produced with an on-time ratio of the direction in which the deformation amount of the reflective surface of the deformable mirror increases toward the intended shape compared to the deformation amount with the on-time ratio for producing the steady-state voltage.

6. The deformable mirror device of claim 1, wherein the voltage control circuit is a control circuit that controls the applied voltage to the deformable mirror with a DC voltage and has a reversing circuit for reversing the polarity of the load, and the transient voltage is of the direction in which the deformation amount of the reflective surface of the deformable mirror increases toward the predetermined shape compared to the deformation amount with the applied DC voltage for producing the steady-state voltage.

7. The deformable mirror device of claim 1, wherein the voltage control circuit is: a control circuit that controls the applied voltage to the deformable mirror with a DC voltage and has a reversing circuit for reversing the polarity of the load and a switching element that turns on and off the DC voltage; and
    a control circuit that performs pulse width modulation by applying on- and off-control signals to the switching element for positive or negative, where the transient voltage is produced with an on-time ratio of the direction in which the deformation amount of the reflective surface of the deformable mirror increases compared to the deformation amount with the on-time ratio for producing the steady-state voltage.

8. The deformable mirror device of claim 1, wherein the transient voltage uses, as the time for applying a voltage of the direction in which the deformation amount of the reflective surface of the deformable mirror increases toward the predetermined shape, a time determined from a time constant of the reflective surface of the deformable mirror to shift a shape of the reflective surface of the deformable mirror to a state near the predetermined shape, and then causes voltage control using the steady-state voltage to start.

9. The deformable mirror device of claim 2, wherein the transient voltage uses, as the time for applying a voltage of the direction in which the deformation amount of the reflective surface of the deformable mirror increases toward the predetermined shape, a time determined from a time constant of the reflective surface of the deformable mirror to shift a shape of the reflective surface of the deformable mirror to a state near the predetermined shape, and then causes voltage control using the steady-state voltage to start.

10. The deformable mirror device of claim 3, wherein the transient voltage uses, as the time for applying a voltage of the direction in which the deformation amount of the reflective surface of the deformable mirror increases toward the intended shape, a time determined from a time constant of the reflective surface of the deformable mirror to shift a shape of the reflective surface of the deformable mirror to a state near the intended shape, and then causes voltage control using the steady-state voltage to start.

11. The deformable mirror device of claim 4, wherein the transient voltage uses, as the time for applying a voltage of the direction in which the deformation amount of the reflective surface of the deformable mirror increases toward the intended shape, a time determined from a time constant of the reflective surface of the deformable mirror to shift a shape of the reflective surface of the deformable mirror to a state near the intended shape, and then causes voltage control using the steady-state voltage to start.

12. The deformable mirror device of claim 5, wherein the transient voltage uses, as the time for applying a voltage of the direction in which the deformation amount of the reflective surface of the deformable mirror to increases toward the intended shape, a time determined from a time constant of the reflective surface of the deformable mirror to shift a shape of the reflective surface of the deformable mirror to a state near the intended shape, and then causes voltage control using the steady-state voltage to start.

13. The deformable mirror device of claim 6, wherein the transient voltage uses, as the time for applying a voltage of the direction in which the deformation amount of the reflective surface of the deformable mirror increases toward the predetermined shape, a time determined from a time constant of the reflective surface of the deformable mirror to shift a shape of the reflective surface of the deformable mirror to a state near the predetermined shape, and then causes voltage control using the steady-state voltage to start.

14. The deformable mirror device of claim 7, wherein the transient voltage uses, as the time for applying a voltage of the direction in which the deformation amount of the reflective surface of the deformable mirror increases toward the predetermined shape, a time determined from a time constant of the reflective surface of the deformable mirror to shift a shape of the reflective surface of the deformable mirror to a state near the predetermined shape, and then causes voltage control using the steady-state voltage to start.

15. A device for observing the retina of an eye, using the deformable mirror device of claim 1.

16. A device for observing the retina of an eye, using the deformable mirror device of claim 2.

17. A device for observing the retina of an eye, using the deformable mirror device of claim 3.

18. A device for observing the retina of an eye, using the deformable mirror device of claim 4.

19. A device for observing the retina of an eye, using the deformable mirror device of claim 5.

20. A device for observing the retina of an eye, using the deformable mirror device of claim 6.

21. A device for observing the retina of an eye, using the deformable mirror device of claim 7.

22. A device for observing the retina of an eye, using the deformable mirror device of claim 8.

* * * * *